United States Patent
Lec et al.

(10) Patent No.: US 11,667,873 B2
(45) Date of Patent: Jun. 6, 2023

(54) ENZYMATIC METHOD FOR REMOVING SULPHITE

(71) Applicant: Université de Lorraine, Nancy (FR)

(72) Inventors: Jean-Christophe Lec, Vandoeuvre-lès-Nancy (FR); Alexandre Kriznik, Villers-lès-Nancy (FR); François Talfournier, Flavigny-sur-Moselle (FR); Sandrine Boschi, Jouy-Aux-Arches (FR)

(73) Assignee: UNIVERSITÉ DE LORRAINE, Nancy (FR)

( * ) Notice: Subject to any disclaimer, the term of this patent is extended or adjusted under 35 U.S.C. 154(b) by 955 days.

(21) Appl. No.: 16/477,001

(22) PCT Filed: Dec. 22, 2017

(86) PCT No.: PCT/FR2017/053822
§ 371 (c)(1),
(2) Date: Jul. 10, 2019

(87) PCT Pub. No.: WO2018/130760
PCT Pub. Date: Jul. 19, 2018

(65) Prior Publication Data
US 2019/0352588 A1 Nov. 21, 2019

(30) Foreign Application Priority Data
Jan. 11, 2017 (FR) ...................................... 1750239

(51) Int. Cl.
*C12G 1/04* (2006.01)
*C12H 1/00* (2006.01)

(52) U.S. Cl.
CPC ............... *C12G 1/04* (2013.01); *C12H 1/003* (2013.01); *C12G 2200/15* (2013.01); *C12Y 208/01002* (2013.01)

(58) Field of Classification Search
CPC ...... C12G 1/04; C12G 2200/15; C12H 1/003; A61P 43/00
See application file for complete search history.

(56) References Cited

U.S. PATENT DOCUMENTS 5,071,664 A 12/1991 Brown

FOREIGN PATENT DOCUMENTS

EP 2090647 A1 8/2009
JP 61074565 A 4/1986
(Continued)

OTHER PUBLICATIONS

International Search Report for international Application No. PCT/FR2017/053822 filed on Dec. 22, 2017; dated Apr. 13, 2018; 3 pages.
(Continued)

*Primary Examiner* — Vera Stulii
(74) *Attorney, Agent, or Firm* — Cantor Colburn LLP

(57) ABSTRACT

The present invention relates to an enzymatic method for removing sulphite. In particular, the present invention relates to a method for converting sulphite present in a composition into thiosulphate, comprising the introduction of 3-mercaptopyruvate sulphurtransferase (3-MST) and a substrate of said 3-mercaptopyruvate sulphurtransferase into said composition. The present invention can be used in particular in the pharmaceutical, cosmetic, food and chemical fields, and any field involving the use of sulphite.

15 Claims, 8 Drawing Sheets

Specification includes a Sequence Listing.

(56) References Cited

FOREIGN PATENT DOCUMENTS

| WO | 8304261 | 12/1983 |
| WO | 2015051187 | 4/2015 |
| WO | 2005107479 | 11/2015 |

OTHER PUBLICATIONS

Jarabak, Rebecca et al., "3-Mercaptopyruvate sulfurtransferase: rapid equilibrium-ordered mechanism with cyanide as the acceptor substrate", Biochemistry, vol. 19, No. 5; Mar. 4, 1980; pp. 900-904.

Written Opinion of the International Searching Authority for International Application No. PCT/FR2017/053822 filed on Dec. 22, 2017; dated Apr. 13, 2018; 5 pages.

Yuka, Kimura et al., "Identification of H2S3 and H2S produced by 3-mercaptopyruvate sulfurtransferase in the brain", Scientific Reports, vol. 5, No. 1; Oct. 6, 2015; pp. 1-11.

Jiten, S.; Definition of "3-mercaptopyruvate sulfurtransferase"; Biochemical Dictionary, 3rd Edition; 1998; p. 1414.

Tanabe, S.; "Development of Assay Methods for Endogenous Inorganic Sulfur Compounds and Sulfurtransferases and Evaluation of rht Physiological Functions of Bound Sulfur"; Yakugaku Zasshi, vol. 128, Issue No. 6; 2008; pp. 881-900.

Valentine, William N. et al., "3-Mercaptopyruvate Sulfurtransferase (EC 2.8.1.2): A Simple Assay Adapted to Human Blood Cells", Clinica Chimica Acta, 1974, vol. 51, No. 2, pp. 205-210.

Andersson, E. et al.; "Cancer incidence among Swedish pulp and paper mill workers: a cohort study of sulphate and sulphite mills"; International Archives of Occupational and Environmental Health, vol. 86; 2013; pp. 529-540; doi: 10.1007/s00420-012-0785-1.

Anonymous; "Select Committee on GRAS Substances (SCOGS) Opinion: Sodium thiosulfate"; Retrieved from URL: http://wayback.archive-it.org/7993/20171031062141/https:www.fda.gov/Food/IngredientsPackagingLabeling/GRAS/SCOGS/ucm261420.htm on Sep. 2, 2022; 1975; 2 pages.

Arrestier, R. et al.; "Successful Treatment of Lung Calciphylazis with Sodium Thiosulfate in a Patient with Sickle Cell Disease: A Case Report"; Medicine, vol. 95, Issue No. 6; 2016; 4 pages; DOI:10.1097/MD.0000000000002768.

Beutler, H.; "Sulphite"; Inorganic Compounds, Chapter. 5; 1988; pp. 585-591.

Hermann, B., et al.; "The octaheme McсA is a haem c-copper sulfite reductase"; Nature, vol. 520, Issue No. 7549; 2015; pp. 706-709; doi:10.1038/nature14109.

Ozsoy, O., et al.; "The effect of ingested sulfite on visual evoked potentials, lipid peroxidation, and antioxidant status of brain in normal and sulfite oxidase-deficient aged rats"; Toxicology and Industrial Health, vol. 32, Issue No. 7; 2014; 11 pages; DOI: 10.1177/0748233714552688.

Shih, V. et al.; "Sulfite Oxidase Deficiency—Biochemical and Clinical Investigations of a Hereditary Metabolic Disorder in Sulfur Metabolism"; The New England Journal of Medicine, vol. 297, Issue No. 19; 1977; pp. 1022-1028.

Bondet al.; "Quantitative analysis of SO2 using the Franz-Paul method"; Quantitative Analysys of Exogenous Compounds; 2005; pp. 137-141.

Grignard, et al.; "Chemical Properties"; Organic Chemistry Treatise; 1950; pp. 769-770.

Figure 10

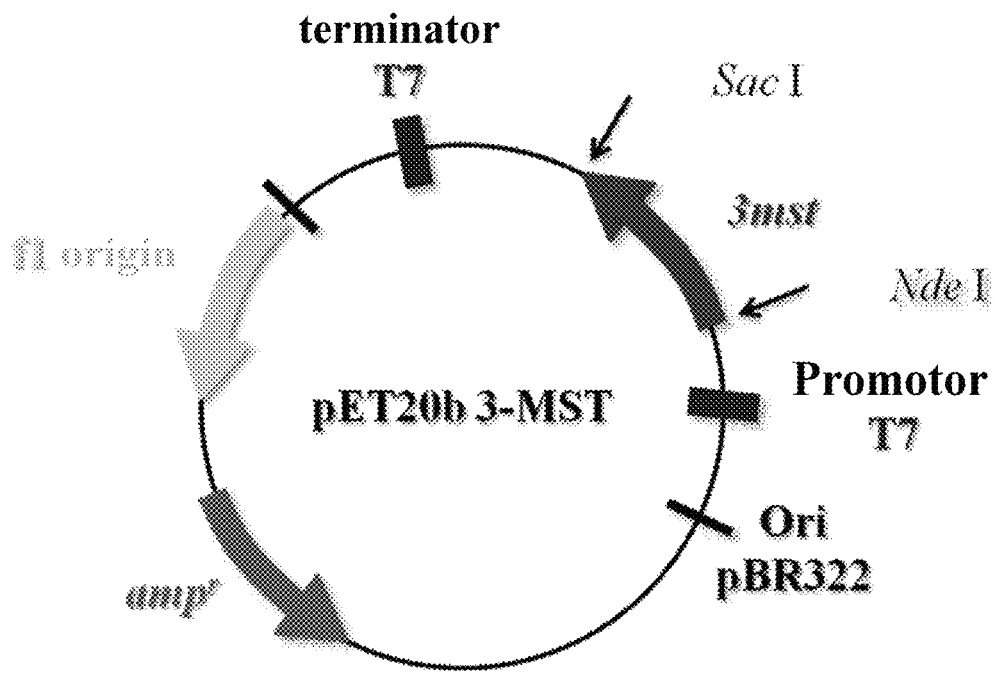

Figure 11

>gi|556503834:2652494-2653339 Escherichia coli str. K-12 substr. MG1655, complete genome.

ATGTCCACGACATGGTTTGTAGGAGCCGACTGGCTCGCCGAACATATTGATGACCCGGAA
ATTCAGATTATCGATGCCCGCATGGCGTCGCCTGGACAGGAGGATCGTAACGTTGCTCAG
GAGTATCTGAATGGACATATTCCCGGCGCAGTGTTTTTTGATATCGAAGCGCTTTCTGATC
ACACTTCCCCGCTTCCGCACATGCTGCCGCGCCCGGAAACGTTCGCCGTGGCGATGCGTG
AATTAGGCGTTAACCAGGATAAGCACCTGATTGTCTATGACGAAGGTAATCTTTTCTCAG
CCCCACGAGCATGGTGGATGCTGCGCACCTTTGGTGTAGAGAAAGTGTCGATTCTGGGGG
GTGGACTTGCAGGCTGGCAGCGCGATGATCTGCTGTTAGAAGAAGGTGCAGTAGAGCTG
CCGGAAGGAGAGTTTAACGCCGCGTTTAATCCTGAAGCCGTGGTGAAAGTAACCGATGTA
TTATTGGCAAGCCATGAAAATACGGCGCAAATTATTGATGCCCGCCCGGCTGCACGTTTT
AACGCAGAAGTTGATGAACCTCGCCCAGGTTTACGTCGCGGACATATTCCCGGAGCACTG
AATGTTCCGTGGACGGAACTGGTGCGCGAAGGCGAACTAAAAACGACCGATGAACTGGA
TGCGATATTTTTTGGTCGCGGCGTCAGCTACGACAAACCAATTATCGTCAGCTGCGGCTCT
GGTGTAACGGCAGCCGTGGTTTTGTTAGCACTCGCGACGCTGGATGTGCCAAACGTGAAA
CTGTACGACGGCGCATGGAGTGAATGGGGCGCGCGGGCAGATTTACCGGTTGAGCCAGT
GAAATAA (SEQ ID NO 1)

Figure 12

>sp|P31142|THTM_ECOLI 3-mercaptopyruvate sulfurtransferase OS=Escherichia coli (strain K12) GN=sseA PE=1 SV=3.

MSTTWFVGADWLAEHIDDPEIQIIDARMASPGQEDRNVAQEYLNGHIPGAVFFDIEALSDHTS
PLPHMLPRPETFAVAMRELGVNQDKHLIVYDEGNLFSAPRAWWMLRTFGVEKVSILGGGLA
GWQRDDLLLEEGAVELPEGEFNAAFNPEAVVKVTDVLLASHENTAQIIDARPAARFNAEVDE
PRPGLRRGHIPGALNVPWTELVREGELKTTDELDAIFFGRGVSYDKPIIVSCGSGVTAAVVLLA
LATLDVPNVKLYDGAWSEWGARADLPVEPVK (SEQ ID NO 2)

Figure 13

(a) Forward primer
GCCGAACATATTGATGCGCCGGAAATTCAGATT (SEQ ID NO 3)

(b) Reverse primer
AATCTGAATTTCCGGCGCATCAATATGTTCCGC (SEQ ID NO 4)

```
                            SEQUENCE LISTING

<160> NUMBER OF SEQ ID NOS: 15

<210> SEQ ID NO 1
<211> LENGTH: 846
<212> TYPE: DNA
<213> ORGANISM: Escherichia coli

<400> SEQUENCE: 1
atgtccacga catggtttgt aggagccgac tggctcgccg aacatattga tgacccggaa      60
attcagatta tcgatgcccg catggcgtcg cctggacagg aggatcgtaa cgttgctcag     120
gagtatctga tggacatat  tcccggcgca gtgttttttg atatcgaagc gctttctgat     180
cacacttccc cgcttccgca catgctgccg cgcccggaaa cgttcgccgt ggcgatgcgt     240
gaattaggcg ttaaccagga taagcacctg attgtctatg acgaaggtaa tcttttctca     300
gccccacgag catggtggat gctgcgcacc tttggtgtag agaaagtgtc gattctgggg     360
ggtggacttg caggctggca gcgcgatgat ctgctgttag aagaaggtgc agtagagctg     420
ccggaaggag agtttaacgc gcgtttaat  cctgaagccg tggtgaaagt aaccgatgta     480
ttattggcaa gccatgaaaa tacggcgcaa attattgatg cccgcccggc tgcacgtttt     540
aacgcagaag ttgatgaacc tcgcccaggt ttacgtcgcg acatattcc  cggagcactg     600 aatgttccgt ggacggaact ggtgcgcgaa ggcgaactaa aaacgaccga tgaactggat     660
gcgatatttt ttggtcgcgg cgtcagctac gacaaaccaa ttatcgtcag ctgcggctct     720
ggtgtaacgg cagccgtggt tttgttagca ctcgcgacgc tggatgtgcc aaacgtgaaa     780
ctgtacgacg gcgcatggag tgaatggggc gcgcgggcag atttaccggt tgagccagtg     840
aaataa                                                               846

<210> SEQ ID NO 2
<211> LENGTH: 281
<212> TYPE: PRT
<213> ORGANISM: Escherichia coli

<400> SEQUENCE: 2

Met Ser Thr Thr Trp Phe Val Gly Ala Asp Trp Leu Ala Glu His Ile
1               5                   10                  15

Asp Asp Pro Glu Ile Gln Ile Ile Asp Ala Arg Met Ala Ser Pro Gly
                20                  25                  30

Gln Glu Asp Arg Asn Val Ala Gln Glu Tyr Leu Asn Gly His Ile Pro
        35                  40                  45

Gly Ala Val Phe Phe Asp Ile Glu Ala Leu Ser Asp His Thr Ser Pro
    50                  55                  60

Leu Pro His Met Leu Pro Arg Pro Glu Thr Phe Ala Val Ala Met Arg
65                  70                  75                  80

Glu Leu Gly Val Asn Gln Asp Lys His Leu Ile Val Tyr Asp Glu Gly
                85                  90                  95

Asn Leu Phe Ser Ala Pro Arg Ala Trp Trp Met Leu Arg Thr Phe Gly
            100                 105                 110

Val Glu Lys Val Ser Ile Leu Gly Gly Gly Leu Ala Gly Trp Gln Arg
        115                 120                 125

Asp Asp Leu Leu Leu Glu Glu Gly Ala Val Glu Leu Pro Glu Gly Glu
    130                 135                 140
```

-continued

Phe Asn Ala Ala Phe Asn Pro Glu Ala Val Lys Val Thr Asp Val
145                 150                 155                 160

Leu Leu Ala Ser His Glu Asn Thr Ala Gln Ile Ile Asp Ala Arg Pro
            165                 170                 175

Ala Ala Arg Phe Asn Ala Glu Val Asp Glu Pro Arg Pro Gly Leu Arg
        180                 185                 190

Arg Gly His Ile Pro Gly Ala Leu Asn Val Pro Trp Thr Glu Leu Val
            195                 200                 205

Arg Glu Gly Glu Leu Lys Thr Thr Asp Glu Leu Asp Ala Ile Phe Phe
210                 215                 220

Gly Arg Gly Val Ser Tyr Asp Lys Pro Ile Ile Val Ser Cys Gly Ser
225                 230                 235                 240

Gly Val Thr Ala Ala Val Val Leu Leu Ala Leu Ala Thr Leu Asp Val
            245                 250                 255

Pro Asn Val Lys Leu Tyr Asp Gly Ala Trp Ser Glu Trp Gly Ala Arg
            260                 265                 270

Ala Asp Leu Pro Val Glu Pro Val Lys
        275                 280

<210> SEQ ID NO 3
<211> LENGTH: 33
<212> TYPE: DNA
<213> ORGANISM: Artificial Sequence
<220> FEATURE:
<223> OTHER INFORMATION: forward primer

<400> SEQUENCE: 3
gccgaacata ttgatgcgcc ggaaattcag att                              33

<210> SEQ ID NO 4
<211> LENGTH: 33
<212> TYPE: DNA
<213> ORGANISM: Artificial Sequence
<220> FEATURE:
<223> OTHER INFORMATION: reverse primer

<400> SEQUENCE: 4
aatctgaatt tccggcgcat caatatgttc cgc                              33

<210> SEQ ID NO 5
<211> LENGTH: 281
<212> TYPE: PRT
<213> ORGANISM: Artificial Sequence
<220> FEATURE:
<223> OTHER INFORMATION: Protein sequence of 3-MST Escherichia coli D17A

<400> SEQUENCE: 5

Met Ser Thr Thr Trp Phe Val Gly Ala Asp Trp Leu Ala Glu His Ile
1               5                   10                  15

Asp Ala Pro Glu Ile Gln Ile Ile Asp Ala Arg Met Ala Ser Pro Gly
            20                  25                  30

Gln Glu Asp Arg Asn Val Ala Gln Glu Tyr Leu Asn Gly His Ile Pro
        35                  40                  45

Gly Ala Val Phe Phe Asp Ile Glu Ala Leu Ser Asp His Thr Ser Pro
    50                  55                  60

Leu Pro His Met Leu Pro Arg Pro Glu Thr Phe Ala Val Ala Met Arg
65                  70                  75                  80

Glu Leu Gly Val Asn Gln Asp Lys His Leu Ile Val Tyr Asp Glu Gly
                85                  90                  95

```
Asn Leu Phe Ser Ala Pro Arg Ala Trp Trp Met Leu Arg Thr Phe Gly
            100                 105                 110

Val Glu Lys Val Ser Ile Leu Gly Gly Leu Ala Gly Trp Gln Arg
        115                 120                 125

Asp Asp Leu Leu Leu Glu Glu Gly Ala Val Glu Leu Pro Gly Gly Glu
    130                 135                 140

Phe Asn Ala Ala Phe Asn Pro Glu Ala Val Val Lys Val Thr Asp Val
145                 150                 155                 160

Leu Leu Ala Ser His Glu Asn Thr Ala Gln Ile Ile Asp Ala Arg Pro
                165                 170                 175

Ala Ala Arg Phe Asn Ala Glu Val Asp Glu Pro Arg Pro Gly Leu Arg
            180                 185                 190

Arg Gly His Ile Pro Gly Ala Leu Asn Val Pro Trp Thr Glu Leu Val
        195                 200                 205

Arg Glu Gly Glu Leu Lys Thr Thr Asp Glu Leu Asp Ala Ile Phe Phe
    210                 215                 220

Gly Arg Gly Val Ser Tyr Asp Lys Pro Ile Ile Val Ser Cys Gly Ser
225                 230                 235                 240

Gly Val Thr Ala Ala Val Val Leu Leu Ala Leu Ala Thr Leu Asp Val
                245                 250                 255

Pro Asn Val Lys Leu Tyr Asp Gly Ala Trp Ser Glu Trp Gly Ala Arg
            260                 265                 270

Ala Asp Leu Pro Val Glu Pro Val Lys
        275                 280

<210> SEQ ID NO 6
<211> LENGTH: 297
<212> TYPE: PRT
<213> ORGANISM: Homo sapiens

<400> SEQUENCE: 6

Met Ala Ser Pro Gln Leu Cys Arg Ala Leu Val Ser Ala Gln Trp Val
1               5                   10                  15

Ala Glu Ala Leu Arg Ala Pro Arg Ala Gly Gln Pro Leu Gln Leu Leu
            20                  25                  30

Asp Ala Ser Trp Tyr Leu Pro Lys Leu Gly Arg Asp Ala Arg Arg Glu
        35                  40                  45

Phe Glu Glu Arg His Ile Pro Gly Ala Ala Phe Phe Asp Ile Asp Gln
    50                  55                  60

Cys Ser Asp Arg Thr Ser Pro Tyr Asp His Met Leu Pro Gly Ala Glu
65                  70                  75                  80

His Phe Ala Glu Tyr Ala Gly Arg Leu Gly Val Gly Ala Ala Thr His
                85                  90                  95

Val Val Ile Tyr Asp Ala Ser Asp Gln Gly Leu Tyr Ser Ala Pro Arg
            100                 105                 110

Val Trp Trp Met Phe Arg Ala Phe Gly His His Ala Val Ser Leu Leu
        115                 120                 125

Asp Gly Gly Leu Arg His Trp Leu Arg Gln Asn Leu Pro Leu Ser Ser
    130                 135                 140

Gly Lys Ser Gln Pro Ala Pro Ala Glu Phe Arg Ala Gln Leu Asp Pro
145                 150                 155                 160

Ala Phe Ile Lys Thr Tyr Glu Asp Ile Lys Glu Asn Leu Glu Ser Arg
                165                 170                 175
```

Arg Phe Gln Val Val Asp Ser Arg Ala Thr Gly Arg Phe Arg Gly Thr
            180                 185                 190

Glu Pro Glu Pro Arg Asp Gly Ile Glu Pro Gly His Ile Pro Gly Thr
            195                 200                 205

Val Asn Ile Pro Phe Thr Asp Phe Leu Ser Gln Glu Gly Leu Glu Lys
            210                 215                 220

Ser Pro Glu Glu Ile Arg His Leu Phe Gln Glu Lys Lys Val Asp Leu
225                 230                 235                 240

Ser Lys Pro Leu Val Ala Thr Cys Gly Ser Gly Val Thr Ala Cys His
                245                 250                 255

Val Ala Leu Gly Ala Tyr Leu Cys Gly Lys Pro Asp Val Pro Ile Tyr
            260                 265                 270

Asp Gly Ser Trp Val Glu Trp Tyr Met Arg Ala Arg Pro Glu Asp Val
            275                 280                 285

Ile Ser Glu Gly Arg Gly Lys Thr His
            290                 295

<210> SEQ ID NO 7
<211> LENGTH: 370
<212> TYPE: PRT
<213> ORGANISM: Leishmania major

<400> SEQUENCE: 7

Met Ser Ala Pro Ala Ala Pro Lys His Pro Gly Lys Val Phe Leu
1               5                   10                  15

Asp Pro Ser Glu Val Lys Asp His Leu Ala Glu Tyr Arg Ile Val Asp
            20                  25                  30

Cys Arg Tyr Ser Leu Lys Ile Lys Asp His Gly Ser Ile Gln Tyr Ala
            35                  40                  45

Lys Glu His Val Lys Ser Ala Ile Arg Ala Asp Val Asp Thr Asn Leu
        50                  55                  60

Ser Lys Leu Val Pro Thr Ser Thr Ala Arg His Pro Leu Pro Pro Cys
65                  70                  75                  80

Ala Glu Phe Ile Asp Trp Cys Met Ala Asn Gly Met Ala Gly Glu Leu
                85                  90                  95

Pro Val Leu Cys Tyr Asp Asp Glu Cys Gly Ala Met Gly Gly Cys Arg
            100                 105                 110

Leu Trp Trp Met Leu Asn Ser Leu Gly Ala Asp Ala Tyr Val Ile Asn
            115                 120                 125

Gly Gly Phe Gln Ala Cys Lys Ala Ala Gly Leu Glu Met Glu Ser Gly
        130                 135                 140

Glu Pro Ser Ser Leu Pro Arg Pro Ala Thr His Trp Pro Phe Lys Thr
145                 150                 155                 160

Ala Phe Gln His His Tyr Leu Val Asp Glu Ile Pro Pro Asn Ala Ile
                165                 170                 175

Ile Thr Asp Ala Arg Ser Ala Asp Arg Phe Ala Ser Thr Val Arg Pro
            180                 185                 190

Tyr Ala Ala Asp Lys Met Pro Gly His Ile Glu Gly Ala Arg Asn Leu
            195                 200                 205

Pro Tyr Thr Ser His Leu Val Thr Arg Gly Asp Gly Lys Val Leu Arg
        210                 215                 220

Ser Glu Glu Glu Ile Arg His Asn Ile Met Thr Val Val Gln Gly Ala
225                 230                 235                 240

Gly Asp Ala Ala Asp Leu Ser Ser Phe Val Phe Ser Cys Gly Ser Gly
                245                 250                 255

Val Thr Ala Cys Ile Asn Ile Ala Leu Val His His Leu Gly Leu Gly
            260                 265                 270

His Pro Tyr Leu Tyr Cys Gly Ser Trp Ser Glu Tyr Ser Gly Leu Phe
        275                 280                 285

Arg Pro Pro Ile Met Arg Ser Ile Ile Asp Asp Tyr Gly Met Cys Met
    290                 295                 300

Gln Met Gln Thr Pro Ser Leu Gly Asp Asn Pro Lys Ala Asn Leu Asp
305                 310                 315                 320

Thr Met Thr Leu Lys Val Asp Gly Ala Pro Cys Glu Arg Pro Asp Ala
                325                 330                 335

Glu Val Gln Ser Ala Ala Thr His Leu His Ala Gly Glu Ala Ala Thr
            340                 345                 350

Val Tyr Phe Lys Ser Gly Arg Val Val Thr Ile Glu Val Pro Ala Val
        355                 360                 365

Pro Asn
    370

<210> SEQ ID NO 8
<211> LENGTH: 846
<212> TYPE: DNA
<213> ORGANISM: Artificial Sequence
<220> FEATURE:
<223> OTHER INFORMATION: Sequence of the 3mst D17A Escherichia coli gene

<400> SEQUENCE: 8
atgtccacga catggtttgt aggagccgac tggctcgccg aacatattga tgcgccggaa        60
attcagatta tcgatgcccg catggcgtcg cctggacagg aggatcgtaa cgttgctcag       120
gagtatctga atggacatat tcccggcgca gtgttttttg atatcgaagc gctttctgat       180
cacacttccc cgcttccgca catgctgccg cgcccggaaa cgttcgccgt ggcgatgcgt       240
gaattaggcg ttaaccagga taagcacctg attgtctatg acgaaggtaa tcttttctca       300
gccccacgag catggtggat gctgcgcacc tttggtgtag agaaagtgtc gattctgggg       360
ggtggacttg caggctggca gcgcgatgat ctgctgttag aagaaggtgc agtagagctg       420
ccggaaggag agtttaacgc gcgtttaat cctgaagccg tggtgaaagt aaccgatgta       480
ttattggcaa gccatgaaaa tacggcgcaa attattgatg cccgcccggc tgcacgtttt       540
aacgcagaag ttgatgaacc tcgcccaggt ttacgtcgcg acatattcc cggagcactg       600 aatgttccgt ggacggaact ggtgcgcgaa ggcgaactaa aaacgaccga tgaactggat       660
gcgatatttt ttggtcgcgg cgtcagctac gacaaaccaa ttatcgtcag ctgcggctct       720
ggtgtaacgg cagccgtggt tttgttagca ctcgcgacgc tggatgtgcc aaacgtgaaa       780
ctgtacgacg gcgcatggag tgaatggggc gcgcgggcag atttaccggt tgagccagtg       840
aaataa                                                                 846

<210> SEQ ID NO 9
<211> LENGTH: 846
<212> TYPE: DNA
<213> ORGANISM: Artificial Sequence
<220> FEATURE:
<223> OTHER INFORMATION: Sequence of the 3mst Escherichia coli gene for
      production in E. coli host

<400> SEQUENCE: 9

```
atgagcacca cctggtttgt tggtgcagat tggctggcag aacatattga tgatccggaa      60
attcagatta tcgatgcacg tatggcaagt ccgggtcaag aagatcgtaa cgttgcacaa     120
gaatatctga atggtcatat tccgggtgcc gtgttttttg atattgaagc actgagcgat     180
cataccagtc cgctgccgca tatgctgcct cgtccggaaa cctttgcagt tgcaatgcgt     240
gaactgggtg ttaatcagga taaacatctg atcgtgtatg atgaaggtaa cctgtttagc     300
gcaccgcgtg catggtggat gctgcgtacc tttggtgttg aaaaagttag cattttaggt     360
ggtggtctgg caggttggca gcgtgatgat ctgctgctgg aagaaggtgc agttgaactg     420
ccggaaggtg aatttaatgc agcatttaat ccggaagccg ttgttaaagt taccgatgtt     480
ctgctggcaa gccatgaaaa ataccgcacag atcattgatg cccgtccggc agcacgtttt     540
aatgccgaag ttgatgaacc gcgtccgggt ctgcgtcgtg gccatattcc tggcgcactg     600
aatgttccgt ggaccgaact ggttcgtgaa ggtgaactga aaaccaccga tgaactggat     660
gcaatctttt ttggtcgtgg tgtgagctat gataaaccga ttattgttag ctgtggtagc     720
ggtgttaccg cagcagttgt gctgctggca ctggcaaccc tggatgttcc gaatgttaaa     780
ctgtatgatg gtgcatggtc agaatggggt gcacgtgccg atctgccggt tgaaccggtt     840
aaataa                                                                846
```

<210> SEQ ID NO 10
<211> LENGTH: 846
<212> TYPE: DNA
<213> ORGANISM: Artificial Sequence
<220> FEATURE:
<223> OTHER INFORMATION: Sequence of the 3mst D17A Escherichia coli gene for production in E. coli host

<400> SEQUENCE: 10

```
atgagcacca cctggtttgt tggtgcagat tggctggcag aacatattga tgcgccggaa      60
attcagatta tcgatgcacg tatggcaagt ccgggtcaag aagatcgtaa cgttgcacaa     120
gaatatctga atggtcatat tccgggtgcc gtgttttttg atattgaagc actgagcgat     180
cataccagtc cgctgccgca tatgctgcct cgtccggaaa cctttgcagt tgcaatgcgt     240
gaactgggtg ttaatcagga taaacatctg atcgtgtatg atgaaggtaa cctgtttagc     300
gcaccgcgtg catggtggat gctgcgtacc tttggtgttg aaaaagttag cattttaggt     360
ggtggtctgg caggttggca gcgtgatgat ctgctgctgg aagaaggtgc agttgaactg     420
ccggaaggtg aatttaatgc agcatttaat ccggaagccg ttgttaaagt taccgatgtt     480
ctgctggcaa gccatgaaaa ataccgcacag atcattgatg cccgtccggc agcacgtttt     540
aatgccgaag ttgatgaacc gcgtccgggt ctgcgtcgtg gccatattcc tggcgcactg     600
aatgttccgt ggaccgaact ggttcgtgaa ggtgaactga aaaccaccga tgaactggat     660
gcaatctttt ttggtcgtgg tgtgagctat gataaaccga ttattgttag ctgtggtagc     720
ggtgttaccg cagcagttgt gctgctggca ctggcaaccc tggatgttcc gaatgttaaa     780
ctgtatgatg gtgcatggtc agaatggggt gcacgtgccg atctgccggt tgaaccggtt     840
aaataa                                                                846
```

<210> SEQ ID NO 11
<211> LENGTH: 894
<212> TYPE: DNA
<213> ORGANISM: Homo sapiens

<400> SEQUENCE: 11

```
atggcttcgc cgcagctctg ccgcgcgctg gtgtcggcgc aatgggtggc ggaggcgctg      60
cgggccccgc gcgctgggca gcctctgcag ctgctggacg cctcctggta cctgccgaag     120
ctggggcgcg acgcgcgacg cgagttcgag gagcgccaca tcccgggcgc cgctttcttc     180
gacatcgacc agtgcagcga ccgcacctcg ccctacgacc acatgctgcc gggggccgag     240
catttcgcgg agtacgcagg ccgcctgggc gtgggcgcgg ccacccacgt cgtgatctac     300
gacgccagcg accagggcct ctactccgcc ccgcgcgtct ggtggatgtt ccgcgccttc     360
ggccaccacg ccgtgtcact gcttgatggc ggcctccgcc actggctgcg ccagaacctc     420
ccgctcagct ccggcaagag ccaacctgct cccgccgagt ccgcgctca gctcgacccc      480
gccttcatca agacctacga ggacatcaag gagaacctgg aatcccggcg cttccaggtg     540
gtggactccc gagccactgg caggttccgc ggcaccgagc ccgagccccg agacggcatt     600
gaacctggcc acatcccagg taccgtgaac atccccttca cagacttcct gagccaggag     660
gggctggaga gagccctga ggagatccgc catctgttcc aggagaagaa agtggacctg      720
tctaagccac tggtggccac gtgtggctct ggcgtcacag cctgccacgt ggcactaggg     780
gcctacctct gcggcaagcc agacgtgccc atctacgatg gctcctgggt ggagtggtac     840
atgcgcgccc ggcccgagga tgtcatctca gagggccggg ggaagaccca ctga          894
```

<210> SEQ ID NO 12
<211> LENGTH: 1113
<212> TYPE: DNA
<213> ORGANISM: Leishmania major

<400> SEQUENCE: 12

```
atgtctgctc tgctgctgc gccgaaacac ccgggcaagg tgttcctgga cccgagcgag      60
gtaaaggacc accttgctga gtaccgcatc gtggactgcc ggtacagctt gaagataaag     120
gaccacggca gcatccagta cgcgaaggag cacgtgaaga gcgccatccg cgccgatgtg     180
gatacgaacc tctctaagtt ggtgcccacc agcaccgccc ggcatccgct accgccctgt     240
gctgagttta tcgactggtg catggcgaac gggatggcgg gagagctgcc agtgctctgc     300
tacgatgacg agtgcggcgc catgggtgga tgccgcctgt ggtggatgct gaactctctt     360
ggcgccgacg cgtacgtgat caacggcggc tttcaggcct gcaaggctgc ggggctggag     420
atggagtccg gcgagccctc gtcgctgcca agacccgcaa cgcactggcc cttcaagacg     480
gccttcagc atcactacct tgtggatgaa atcccgccca acgcaatcat caccgacgcg     540
cgctccgccg accgcttcgc ctcgacagta cgaccttacg ccgcagacaa gatgccaggc     600
cacatcgaag tgcgcgtaa cctcccctac acgtcgcacc tcgtgacacg cggtgacggc     660
aaggtgctgc gcagtgagga agagatccgc cacaacatca tgaccgtcgt gcaaggcgcg     720
ggtgacgcgc tgatctatc gagcttcgtc ttctcctgcg gcagcggcgt caccgccctgc    780
atcaatatcg ccctggtgca ccacctcggc ctgggccatc cgtacctcta ctgtggctcc     840
tggtctgagt acagcggcct cttccgcccc cccataatgc gcagcatcat cgacgactac     900
ggcatgtgca tgcaaatgca gaccctagc ctcggcgaca cccgaaggc aaacctcgac       960
accatgacgc tgaaggtcga cggcgcgccc tgcgagagac ccgatgcgga ggtgcagagc    1020
gccgcaaccc acctccacgc tggcgaggcc gctaccgtgt acttcaagag cggccgcgtc    1080
gtcacgatcg aggtgccggc agtgcccaac taa                                1113
```

```
<210> SEQ ID NO 13
<211> LENGTH: 5
<212> TYPE: PRT
<213> ORGANISM: Artificial Sequence
<220> FEATURE:
<223> OTHER INFORMATION: part of the sequence of the 3-mercaptopyruvate
      sulfurtransferase
<220> FEATURE:
<221> NAME/KEY: MISC_FEATURE
<222> LOCATION: (2)..(2)
<223> OTHER INFORMATION: Xaa is A, V or L

<400> SEQUENCE: 13

Arg Xaa Trp Trp Met
1               5

<210> SEQ ID NO 14
<211> LENGTH: 8
<212> TYPE: PRT
<213> ORGANISM: Artificial Sequence
<220> FEATURE:
<223> OTHER INFORMATION: part of the sequence of the 3-mercaptopyruvate
      sulfurtransferase
<220> FEATURE:
<221> NAME/KEY: MISC_FEATURE
<222> LOCATION: (8)..(8)
<223> OTHER INFORMATION: Xaa is A or C

<400> SEQUENCE: 14

Cys Gly Ser Gly Val Thr Ala Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: part of the sequence of 3-mercaptopyruvate
      sulfurtransferase
<220> FEATURE:
<221> NAME/KEY: MISC_FEATURE
<222> LOCATION: (4)..(4)
<223> OTHER INFORMATION: Xaa is P or E

<400> SEQUENCE: 15

Gly His Ile Xaa Gly
1               5
```

ENZYMATIC METHOD FOR REMOVING SULPHITE

CROSS REFERENCE TO RELATED APPLICATIONS

This application is a National Stage application of PCT/FR2017/053822, filed Dec. 22, 2017, which claims the benefit of French Application No. 1750239, filed Jan. 11, 2017, both of which are incorporated by reference in their entirety herein.

TECHNICAL FIELD

The present invention relates to an enzymatic method for removing sulfite. In particular, the present invention relates to a method for converting the sulfite present in a composition into thiosulfate, comprising the introduction of 3-mercaptopyruvate sulfurtransferase (3-MST) and of a substrate of said 3-mercaptopyruvate sulfurtransferase into said composition.

The present invention has applications in particular in the pharmaceutical, cosmetics, agri-food and chemical fields, and any field involving the use of sulfite.

In the description below, the references between square brackets ([ ]) refer to the list of references presented at the end of the text.

PRIOR ART

Sulfite is a compound that is widely used in industry, since it is inexpensive and has a very broad spectrum of actions and/or effects. In particular, sulfite is used for its antioxidant, antiseptic and/or anti-oxidase properties.

By virtue of its use in various technical fields, in particular in the agri-food field, the effect of sulfites and the tolerance thereto by human beings are being increasingly studied. In particular, it has been demonstrated that excessive consumption of sulfite can lead to effects harmful to the health, and can induce intolerance or even toxic effects.

An evaluation of sulfite as a food additive was carried out in 2008 by the WHO which indicated that the total dietary exposure to sulfites differs between countries because of different methods of use of said sulfites in foods and because of the consumption of said foods to which sulfites may be added. It has been shown that they are present in particular in alcoholic drinks, in particular wine, and non-alcoholic drinks, but also in pork meat products, in particular sausages, in dried fruits, in nuts and in processed potatoes.

An acceptable daily intake has been determined and is from 0 to 0.7 mg/kg of body weight (World Health Organization).

The presence of sulfites in the products of everyday life, such as foods and drugs, results in the absorption of large daily amounts capable of causing health problems such as headaches, allergies and asthma for the less serious consequences, ranging up to cardiovascular problems and an increase in the risk of cancer, for example brain and/or liver tumors, for the most serious cases (Shih et al., 1977, The New England Journal of Medicine [1]; Andersson et al., 2013, International Archives of Occupational and Environmental Health [2]; Ozsoy et al., 2014, Toxicology and Industrial Health [3]). In addition, sulfites have been listed as being among the ten priority food allergens (Health Agency, Canadian Government).

The presence of sulfites in agri-food products can now be considered to be a public health problem since approximately one million French people currently have too high an intake (study carried out by Insee [French National Institute of Statistics and Economic Studies] and Anses [French Agency for Food, Environmental and Occupational Health and Safety] in September 2012). Thus, in the context of a French national program (since 2009) financed by FranceAgriMer, coordinated by the IFV (Institut Français de la vigne et du Vin [French Institute for Vines and Wine]) and grouping together several technical partners such as INRA (Institut National de la Recherche Agronomique [French National Institute of Agronomic Research]), research studies have been carried out for many years with the objective of decreasing the final amount of sulfites, in particular in wine.

There is thus a real need to find a means for reducing the amount/the presence of sulfite which overcomes these faults, drawbacks and obstacles of the prior art, in particular a method which makes it possible to control the sulfite contents in compositions regardless of the field, in particular the food, pharmaceutical, etc., field.

There are in the prior art methods/devices which are used/studied/in the process of being tested in order to try to reduce the sulfite content in compositions.

For example, in the wine-producing field, one approach explored is to test various paths/methods of production aimed at decreasing the use of sulfite in wine-making processes, the medium-term objective being to decrease the final concentration of sulfite to between 50 and 100 mg/l (developed by the IFV). Another approach is to try to replace the sulfite with one or more compound(s), for example ascorbic acid, lysozyme or short-chain fatty acids such as sorbic acid. However, these various compounds do not make it possible to reproduce/obtain all of the technical effects of sulfites. Thus, they do not allow an effective replacement, in particular an identical replacement. In addition, they may cause or do cause a modification and detrimental alteration in the properties of the composition and in particular the organoleptic characteristics of compositions, in particular of wine (IFV and INRA).

Another approach explored is the withdrawal/removal of sulfites from compositions, in particular from the final product after production. For example, one strategy consists in using a chromatographic method which makes it possible to bind and therefore remove the sulfite present in wine at the end of the process (WO 2015/051187 [4]). This technique allows the removal of the free sulfites only and could result in the removal of other essential components.

Another strategy consists in using enzymes, for example sulfite oxidase which converts sulfite into sulfate (WO 2015/051187 [4]). However, this reaction is reversible, the equilibrium can be shifted and this method is thus capable of producing sulfite from sulfate. In addition, the stability of sulfite oxidase is relative; in particular, the enzyme is not stable enough for use at low pH as is the case when sulfite is added as a preserving additive. Another enzyme, sulfite reductase, which has a rapid sulfite-removing activity, has been proposed. However, the product obtained is hydrogen sulfide which greatly detrimentally alters the properties of the composition, and in particular the organoleptic properties (Hermann et al., 2015, Nature [5]).

Other methods for the oxidation of sulfites, for example via the addition of compounds and/or of enzymes to the composition, have also been envisioned. However, these methods are limited by virtue of their efficiency and/or the possible detrimental alteration of the properties of the composition, in particular its organoleptic properties.

There is thus a real need to find a means for reducing the amount/presence of sulfites, in particular present in compositions, which overcomes these faults, drawbacks and obstacles of the prior art, in particular a means for removing/reducing the amount of sulfites without negative alterations of the properties of the composition.

DESCRIPTION OF THE INVENTION

The objective of the present invention is specifically to meet this need by providing a 3-mercaptopyruvate sulfurtransferase (3-MST) which very efficiently converts sulfite into thiosulfate.

In particular, the inventors have demonstrated, surprisingly, that a 3-mercaptopyruvate sulfurtransferase (3-MST) makes it possible to convert sulfites into another compound.

The inventors provide in particular a method for treating a composition comprising the introduction of 3-mercaptopyruvate sulfurtransferase (3-MST) and at least one substrate of said 3-mercaptopyruvate sulfurtransferase into said composition.

In other words, the inventors provide a method for treating a composition, comprising the introduction of 3-mercaptopyruvate sulfurtransferase (3-MST) and at least one substrate of said 3-mercaptopyruvate sulfurtransferase into said composition in order to convert sulfites present in said composition.

A subject of the present invention is also a method for converting the sulfite present in a composition, comprising the introduction of 3-mercaptopyruvate sulfurtransferase (3-MST) and of a substrate of said 3-mercaptopyruvate sulfurtransferase into said composition.

The inventors also provide a method for converting the sulfite present in a composition into thiosulfate, comprising the introduction of 3-mercaptopyruvate sulfurtransferase (3-MST) and of a substrate of said 3-mercaptopyruvate sulfurtransferase into said composition.

In particular, the inventors have demonstrated, surprisingly, that 3-mercaptopyruvate sulfurtransferase (3-MST) makes it possible, in the presence of a substrate, to catalyze a reaction converting the sulfite into thiosulfate.

The inventors have also demonstrated, surprisingly, that the conversion of the sulfite into thiosulfate by *Escherichia coli* 3-mercaptopyruvate sulfurtransferase (3-MST) is irreversible.

The inventors have also demonstrated, surprisingly, that the conversion of the sulfite into thiosulfate by 3-mercaptopyruvate sulfurtransferase (3-MST) is an irreversible stoichiometric reaction which advantageously makes it possible to convert a given amount of sulfite and/or all of the sulfites present in the composition. FIG. 1 is a scheme of the enzymatic reaction catalyzed by 3-mercaptopyruvate sulfurtransferase (3-MST) in the presence of 3-mercaptopyruvate (3-MP) and of sulfite.

In the present application, the term "treatment of a composition" is intended to mean the introduction of 3-mercaptopyruvate sulfurtransferase and of a substrate of said 3-mercaptopyruvate sulfurtransferase into a composition in order to convert sulfites present into thiosulfates.

In the present application, the expression "introduction of 3-mercaptopyruvate sulfurtransferase and of a substrate of said 3-mercaptopyruvate sulfurtransferase into the composition" is intended to mean any suitable means, known to those skilled in the art, of introducing 3-mercaptopyruvate sulfurtransferase and a substrate of said 3-mercaptopyruvate sulfurtransferase into the composition. The introduction can be carried out by pouring the 3-mercaptopyruvate sulfurtransferase and its substrate into the composition, by injection into the composition, for example with a device of syringe type, or by spraying the composition. Those skilled in the art, by virtue of their general knowledge, will know how to adapt the introduction of the 3-mercaptopyruvate sulfurtransferase according to the composition to be treated.

In the present application, the 3-mercaptopyruvate sulfurtransferase can be introduced in any suitable form known to those skilled in the art. For example, it can be introduced in the form of a powder, for example a freeze-dried, encapsulated or nonencapsulated, powder; in solution, for example in physiological saline, or in a buffered solution.

In the present application, the substrate of 3-mercaptopyruvate sulfurtransferase can be introduced in any suitable form known to those skilled in the art. For example, it can be introduced in the form of a powder, for example a freeze-dried, encapsulated or nonencapsulated, powder; in solution, for example in physiological saline, or in a buffered solution. In the present application, the 3-mercaptopyruvate sulfurtransferase may be an isolated protein and/or a recombinant protein. It may for example be a 3-mercaptopyruvate sulfurtransferase isolated from an animal, from an insect, from a bacterium, from a fungus, from a plant, from an extremophilic microorganism and/or from an archea. It may be a 3-mercaptopyruvate sulfurtransferase comprising, in its peptide sequence, the following three sequences:

$RX_aWWM$ (SEQ ID No. 13)

$CGSGVTAX_b$ (SEQ ID No. 14)

$GHIX_cG$ (SEQ ID No. 15)

wherein $X_a$ is A, V or L, $X_b$ is A or C, and $X_c$ is P or E.

The inventors have in fact demonstrated that the 3-mercaptopyruvate sulfurtransferases comprise these sequences in common in their respective sequence and are capable of catalyzing the reaction for transfer of sulfur from a donor substrate such as 3-mercaptopyruvate (3-MP) to sulfite by going through a transient persulfide intermediate of the enzyme (FIG. 1). The reaction results in the formation of pyruvate and of thiosulfate: odorless, colorless and nontoxic products.

In the present application, the 3-mercaptopyruvate sulfurtransferase may be a recombinant enzyme comprising one or more mutation(s) in its peptide sequence. It may for example be a 3-mercaptopyruvate sulfurtransferase comprising the replacement of at least one acidic amino acid with a hydrophobic amino acid. The 3-mercaptopyruvate sulfurtransferase may be a recombinant enzyme comprising the replacement of an acidic amino acid, for example aspartic acid or glutamic acid, with an amino acid comprising a hydrophobic side chain, for example alanine, valine, isoleucine, methionine, phenylalanine, tyrosine, methionine and/or tryptophan. It may for example be an *Escherichia coli* 3-mercaptopyruvate sulfurtransferase comprising a substitution, in position 17 of its peptide sequence, of the aspartic acid by an alanine. It may for example be the 3-mercaptopyruvate sulfurtransferase of sequence SEQ ID No. 2, 5, 6 or 7 of the appended sequence listing and/or a protein of which the sequence comprises the peptides of sequences SEQ ID Nos 13, 14 and 15.

The inventors have demonstrated, surprisingly, that the substitution of the aspartic acid in position 17 of *Escherichia coli* 3-mercaptopyruvate sulfurtransferase by an alanine advantageously makes it possible to increase the enzyme production yield. For example, in the case of a production in

*Escherichia coli* cells, the production/purification yield of this D17A mutant is greater by a factor of 10 than that of the wild-type form of the enzyme.

In the present invention, the 3-mercaptopyruvate sulfurtransferase can be obtained from a nucleotide sequence encoding the 3-mercaptopyruvate sulfurtransferase used in the present invention, for example the proteins of which the sequence comprises the peptides of sequences SEQ ID Nos 13, 14 and 15, the peptide of sequence chosen from the group comprising the proteins of sequence SEQ ID No. 2, 5, 6 or 7. It may for example be a nucleic acid comprising or consisting of the sequence chosen from the group comprising the sequences SEQ ID Nos 1, 8, 9, 10, 11 and 12.

In the present invention, the nucleotide sequence(s) encoding the 3-mercaptopyruvate sulfurtransferase may be contained independently in an expression vector suitable for their expression.

In the present invention, a vector comprising a nucleotide sequence encoding one of the 3-mercaptopyruvate sulfurtransferases used in the present invention, for example a nucleotide sequence chosen from the group comprising the sequences SEQ ID Nos 1, 8, 9, 10, 11 and 12. The vector may be one of the vectors known to those skilled in the art and for producing recombinant proteins. It is generally chosen in particular as a function of the cell host used. The vector may for example be chosen from the vectors listed in the catalog http://www.promega.com/vectors/mammalian_express-_vectors.htm [6] or
http://www.qiagen.com/overview/
qiagenes.aspx?gaw=PROTQIAgenes080
7&gkw=mammalian+expression [7], or else
http://www.scbt.com/
chap_exp_vectors.php?type=pCruzTM%20Expression%
20Vectors [8]. It may for example be the expression vector described in document WO 83/004261 [9].

The nucleic acids of the present invention or the vectors of the present invention can be used in particular for the production of 3-mercaptopyruvate sulfurtransferase. Thus, the present invention also relates to a host cell comprising a nucleic acid sequence encoding one of the 3-mercaptopyruvate sulfurtransferases or a vector encoding one of the 3-mercaptopyruvate sulfurtransferases.

The host cell or cell host may be any host suitable for the production of the 3-mercaptopyruvate sulfurtransferases of the present invention from the abovementioned vectors comprising a nucleotide sequence encoding a 3-mercaptopyruvate sulfurtransferase according to the invention.

For the purposes of the present invention, the term "host cell" is intended to mean a prokaryotic or eukaryotic cell. Host cells commonly used for the expression of recombinant proteins include, in particular, cells of bacteria such as *Escherichia coli* or *Bacillus* sp., cells of yeasts such as *Saccharomyces cerevisiae*, cells of fungi such as *Aspergillus niger*, insect cells, and mammalian cells (in particular human cells) such as the cell lines HEK 293, PER-C6, CHO, etc. Transformation of the prokaryotic and eukaryotic cells is a technique well known to those skilled in the art, for example lipofection, electroporation, heat shock, or chemical methods. Depending on the cell to be transformed, those skilled in the art will be able to easily determine the means required for the transformation of the chosen host cell. Thus, the expression vector and the method for introducing the expression vector into the host cell will be selected according to the chosen host cell. The host cell transformed by an expression vector will produce a corresponding protein for example in recombinant form. Those skilled in the art can easily verify that the host cell produces the protein, for example the recombinant protein, for example using the Western blot technique.

Thus, the present invention also relates to a method for producing 3-mercaptopyruvate sulfurtransferase by transformation of a host cell using a vector as defined above and incubation of said transformed cell.

In this method, the host cell may be any suitable cell known to those skilled in the art. It may for example be the host cells as defined above.

According to the invention, the transformation can be carried out by any method known to those skilled in the art. The transformation of prokaryotic and eukaryotic cells is a technique well known to those skilled in the art, for example lipofection, electroporation, heat shock or chemical methods. Depending on the cell to be transformed, those skilled in the art will be able to easily determine the means required for the transformation of the chosen host cell.

According to the invention, the incubation can be carried out by any method known to those skilled in the art. The incubation/culture of prokaryotic and eukaryotic cells is a technique well known to those skilled in the art. Depending on the cell, those skilled in the art will be able to easily determine the necessary means, culture medium, time and temperature conditions, required for the incubation/culture of the chosen host cell.

According to the invention, the production method may comprise a step, after transformation and culture/incubation of the transformed cell, of purification of the 3-mercaptopyruvate sulfurtransferase.

The purification of said 3-mercaptopyruvate sulfurtransferase produced can be carried out by any means known to those skilled in the art. It may for example be a technique chosen from electrophoresis, molecular sieving, ultracentrifugation, differential precipitation, for example with ammonium sulfate, ultrafiltration, membrane or gel filtration, ion exchange, separation by hydrophobic interactions, or affinity chromatography, for example of IMAC type.

In the present invention, the amount of 3-mercaptopyruvate sulfurtransferase introduced into the composition may be between 100 and 500 nM, for example from 250 to 500 nM. Of course, those skilled in the art, by virtue of their general knowledge, will know how to adjust the amount of 3-mercaptopyruvate sulfurtransferase to be introduced into the composition.

In the present invention, the method according to the invention may comprise, after the introduction of the 3-mercaptopyruvate sulfurtransferase and of a substrate of said 3-mercaptopyruvate sulfurtransferase, a step of incubation in the composition. In the present invention, the incubation may be carried out for a time of from 1 to 60 min, for example from 1 to 5 min.

In the present invention, the incubation may be carried out at a temperature of from 3 to 35° C., for example from 4 to 30° C.

In the present invention, the composition may be any composition known to those skilled in the art. It may for example be a chemical composition, an agri-food composition, a pharmaceutical composition, a cosmetic composition and/or a veterinary composition.

In the present invention, the composition may be in any liquid form known to those skilled in the art. It may for example be an aqueous solution, an alcoholic solution or an aqueous-alcoholic solution.

In the present invention, the agri-food composition may be any agri-food composition, which is for example liquid, which is known to those skilled in the art and which may comprise sulfites. It may for example be an alcoholic composition, for example white wine, red wine, rosé wine, champagne, beer and/or cider, foods, for example pickles, tomato sauce, ketchup, mustard, jelly, canned fruits, fruit juices, fruit salads, fruit syrups, canned vegetables, vinegar, vinaigrettes and soups. It may also be a composition for cooking foods, for example stock.

In the present invention, the pharmaceutical composition may be any pharmaceutical composition known to those skilled in the art which may comprise sulfites. It may for example be a composition for intravenous administration, an oral composition, a product for application to the skin, and/or any administration known to those skilled in the art in the form of a liquid composition/formulation and/or of hydratable dry compositions, for example a powder to be rehydrated.

In the present invention, the veterinary composition may be any veterinary composition known to those skilled in the art which may comprise sulfites. It may for example be any veterinary composition, which is for example liquid, known to those skilled in the art and/or hydratable dry compositions, for example a powder to be rehydrated.

In the present invention, the cosmetic composition may be any cosmetic composition known to those skilled in the art which may comprise sulfites. It may for example be shower gels or self-tanning agents.

In the present invention, the term "substrate of 3-mercaptopyruvate sulfurtransferase" is intended to mean any substrate known to those skilled in the art. It may for example be 3-mercaptopyruvate or any sulfur-comprising compound which results in the formation of a persulfide intermediate on the 3-mercaptopyruvate sulfurtransferase.

In the present invention, the maximum amount of substrate, for example of 3-mercaptopyruvate, introduced into the composition may correspond to the amount of sulfite present in the composition. In the present invention, the stoichiometric ratio of said substrate to the sulfite present in said composition may be at most 1:1. For example, for 1 l of a composition containing 1.25 mmol of sulfite, the maximum amount of 3-mercaptopyruvate introduced into the composition is 1.25 mmol. Of course, those skilled in the art, by virtue of their general knowledge, will know how to adjust the amount of 3-mercaptopyruvate to be introduced into the composition.

In the present invention, the method according to the invention may comprise, prior to the introduction into a composition of 3-mercaptopyruvate sulfurtransferases and/or of substrates thereof, a prior step of measurement of the concentration and/or amount of sulfites present in the composition.

In the present invention, the measurement of the concentration and/or amount of sulfites present in the composition may be carried out by any suitable method known to those skilled in the art. It may for example be a commercially available method and/or device, for example the SO kit sold by the company Megazyme International, Ireland (Beutler, H. O. (1988). Sulphite In Methods of Enzymatic Analysis [10]) or the Quantofix Sulfit (registered trademark) strips sold by the company Macherey-Nagel. The amount of sulfite may also be determined, prior to the application of said method, by means of conventional methods, for example currently used in the wine making industry, for example the Franz Paul method which is the reference method in enology (Chantal Bonder and Raymond Sylvestre, Pratiquer les contrôles en œnologie [Carrying out tests in enology] [11]), and/or by using chemical kits, for example sold by the company Megazyme International, Ireland.

Those skilled in the art, by virtue of their general knowledge, will know how to adapt the method for measuring the concentration/amount of sulfites as a function of the composition.

In the present invention, the percentage of the molar ratio of 3-mercaptopyruvate introduced into the composition relative to the sulfites present in the composition may be within a range of from 0.01% to 100%, for example from 25% to 100%.

The inventors have demonstrated that the reaction for conversion of sulfite into thiosulfate has a stoichiometry of 1:1 with the amount of 3-mercaptopyruvate. The inventors have also demonstrated that it is possible to convert a given amount of sulfite present in the composition.

In other words, the method of the invention also makes it possible to precisely control the amount of sulfites converted into thiosulfate and also the possible residual amount present in the composition after implementation of the method.

In addition, the method of the invention allows, when the substrate is 3-mercaptopyruvate the, production of pyruvate in the composition. The formation of pyruvate in particular in agri-food, pharmaceutical, cosmetic and veterinary compositions has no effect with regard to the color, odor and/or possible toxicity. In other words, the pyruvate and the thiosulfate resulting from the method are odorless, colorless and non-toxic (FDA report on thiosulfate 223-75-2004, 1975 [12]).

Furthermore, the products resulting from the method do not negatively modify the essential characteristics of the composition, for example its appearance, its taste properties, its olfactory properties.

The method according to the invention also advantageously makes it possible to obtain compositions of which the organoleptic properties are unchanged. In other words, the method according to the invention does not modify the organoleptic properties of the composition to which it is applied.

Furthermore, the method according to the invention allows the production of thiosulfate which advantageously is of use in treatment against calciphylaxis (Arrestier et al., 2016, Medicine [13]). In addition, thiosulfate, by virtue of its antioxidant effect, is of use for alcoholic composition stabilization, for example as used in the United States.

Thus, the invention advantageously makes it possible to improve the stability of the compositions on which it is used.

Other advantages may further emerge to those skilled in the art on reading the examples below, illustrated by the appended figures, given by way of illustration.

BRIEF DESCRIPTION OF THE FIGURES

Figure 10:
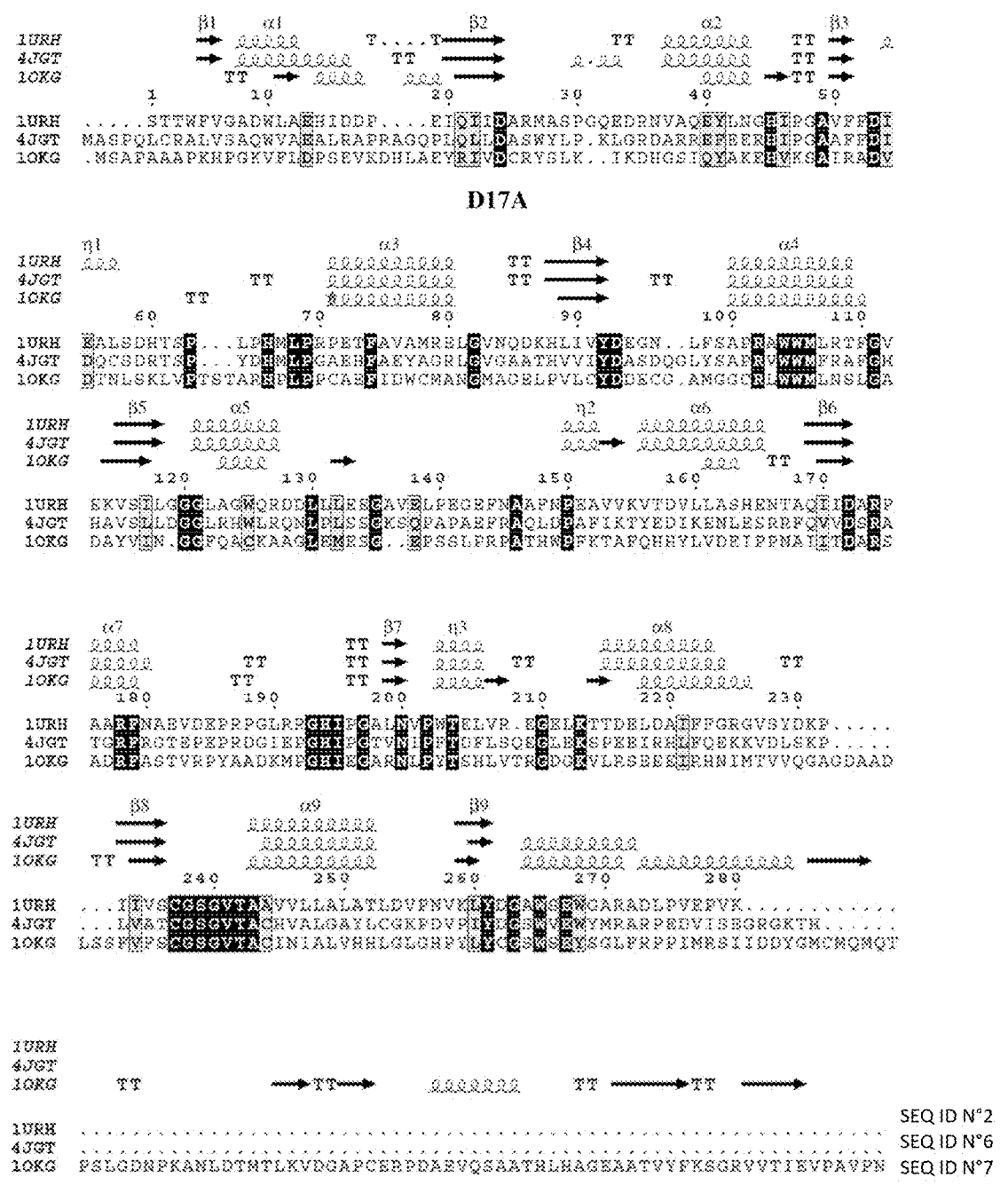

FIG. 10 represents an alignment of protein sequences and of secondary structures of three 3-mercaptopyruvate sulfurtransferases (3-MST): *Escherichia coli* 3-MST (code PDB 1URH), human 3-MST (code PDB 4JGT) and *Leishmania major* 3-MST (code PDB 1OKG) demonstrating the conserved amino acids and the position of the amino acid (Aspartate 17) that has been mutated to alanine.

FIG. 11 represents a scheme of the pET20b 3-MST vector used for the production of the wild-type form and of the D17A mutant of the *Escherichia coli* 3-mercaptopyruvate sulfurtransferase. The pET20b 3-MST construct is a recombinant vector obtained from the commercial pET20b, Invitrogen (registered trade mark).

FIG. 12 corresponds to the sequence of the coding region of the *Escherichia coli* 3mst gene. The mutated codon which makes it possible to obtain the D17A mutant of *Escherichia coli* 3-mercaptopyruvate sulfurtransferase is underlined and highlighted in gray.

FIG. 13 is the protein sequence of the wild-type form of *Escherichia coli* 3-mercaptopyruvate sulfurtransferase. The aspartic acid underlined and highlighted in gray corresponds to the amino acid mutated to alanine in the D17A mutant of *Escherichia coli* 3-mercaptopyruvate sulfurtransferase.

FIG. 14 contains the sequence of the forward (a) and reverse (b) nucleotide primers used during the site-directed mutagenesis carried out on the pET20b 3-MST expression vector.

EXAMPLES

Figure 1:
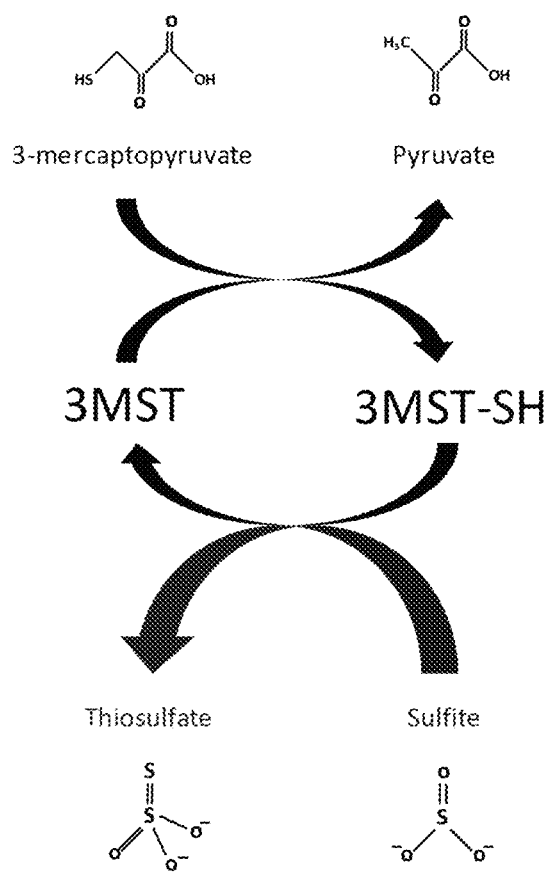
FIG. 1 is a scheme representing the catalytic mechanism of 3-mercaptopyruvate sulfurtransferase in which 3-mercaptopyruvate is used as sulfur-donating substrate and sulfite is used as acceptor resulting in the formation of pyruvate and of thiosulfate.

Example 1: Production and Purification of *Escherichia coli* 3-Mercaptopyruvate Sulfurtransferase D17A The plasmid encoding *Escherichia coli* 3-mercaptopyruvate sulfurtransferase D17A was obtained by site-directed mutagenesis of the plasmid encoding the wild-type form of the enzyme (FIGS. 11, 12, 13 and 14).

The D17A mutant of *Escherichia coli* 3-mercaptopyruvate sulfurtransferase was produced by transformation of *Escherichia coli* BL21(DE3) bacteria with a pET20b 3-MST expression vector. The transformation of 50 µl of BL21 (DE3) competent cells with 100 ng of pET20b 3-MST was carried out by incubating the mixture in ice for 30 min, followed by a heat shock (30 seconds at 42° C.). The mixture was then used to inoculate a preculture of 50 ml of LB medium supplemented with ampicillin (200 mg/l). After overnight incubation at 37° C. with shaking, 4 l of LB medium supplemented with ampicillin (200 mg/l) were inoculated at 1/100 and placed at 37° C. with shaking. When the optical density at 600 nm reached 0.6, the expression was induced by adding 1 mM of IPTG (isopropyl-1-thio-β-D-galactopyranoside). The cells were then placed at 37° C. for 3 hours with shaking, then harvested by centrifugation at 3000 g. The cell pellets were taken up in 20 ml of TE buffer 50 mM Tris HCl, 2 mM EDTA, pH 8) containing 10 mM of DTT, 20 U/ml of benzonase and 4 mM of $MgSO_4$. The cell lysis was carried out by sonication at 4° C. at a power of 40 W per period of two times 2 minutes for 50% of the time. The cell debris was removed by centrifugation at 17 000 g for 45 minutes.

The enzyme was purified by means of a protocol comprising the following three steps:
Precipitation with ammonium sulfate: The soluble fraction obtained after sonication was brought to 65% ammonium sulfate (AS) saturation with gentle stirring at 4° C. At this concentration, the protein precipitated and, after centrifugation at 17 000 g for 45 minutes, the pellet was then taken up in 20 ml of TE buffer (50 mM Tris HCl, 2 mM EDTA, pH 8).
Phenyl-Sepharose hydrophobic interaction chromatography (GE Healthcare (registered trademark)): Ammonium sulfate was gradually added to the protein solution until a concentration of 1 M was obtained. This solution was then filtered (0.2 µm) before injection onto a Phenyl-Sepharose hydrophobic interaction column pre-equilibrated with TE buffer, 1M AS. The elution was carried out by decreasing gradient of ammonium sulfate (from 1 to 0 M). The fractions collected were analyzed by SDS-12.5% PAGE electrophoresis and those containing the 3-mercaptopyruvate sulfurtransferase were combined and then dialyzed overnight against TE buffer (50 mM Tris HCl, 2 mM EDTA, pH 8).

Q-Sepharose anion exchange chromatography (GE Healthcare (registered trademark)): After dialysis, the protein solution was filtered at 0.2 µm and then injected onto a Q-Sepharose anion exchange chromatography column pre-equilibrated with TE buffer (GE Healthcare (registered trade mark)). The elution was carried out by applying an increasing gradient of KCl (0 to 1 M). The fractions containing the 3-mercaptopyruvate sulfurtransferase were identified by SDS-12.5% PAGE electrophoresis and then combined and concentrated by ultrafiltration on an Amicon cell using a YM 10 membrane (10 kDa threshold). The protein solution thus purified was brought to an ammonium sulfate saturation of 70% in order to precipitate the protein and to store it at −20° C. in the presence of 5 mM of DTT.

Figure 2:
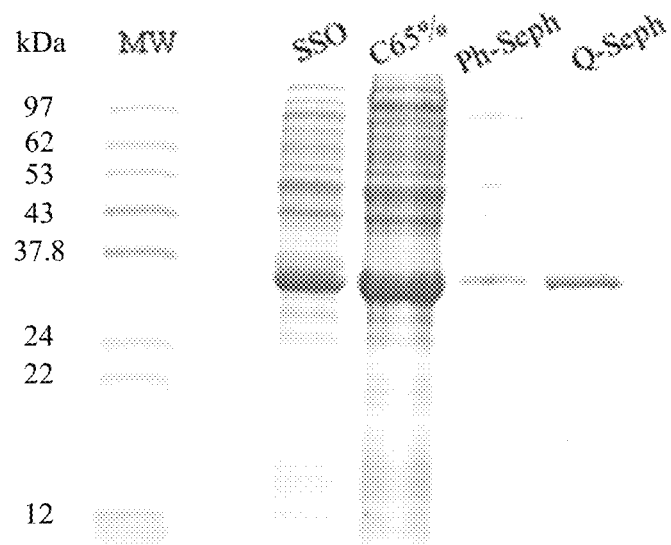
FIG. 2 is a photograph of an SDS-12.5% PAGE protein gel showing the various steps of purification of *Escherichia coli* 3-mercaptopyruvate sulfurtransferase. The MW column corresponds to the molecular weight markers, the SSO column corresponds to the soluble fraction obtained after bacterial cell lysis, the C65% column corresponds to the insoluble fraction obtained after precipitation in the presence of 65% ammonium sulfate, the Ph-Seph column corresponds to the fraction obtained after Phenyl-Sepharose hydrophobic interaction chromatography (GE Healthcare (registered trade mark)) and the Q-Seph column corresponds to the fraction obtained after Q-Sepharose anion exchange chromatography (GE Healthcare (registered trade mark)).

FIG. 2 is a photograph of an SDS-12.5% PAGE protein gel after migration of the samples obtained after each of the *Escherichia coli* 3-mercaptopyruvate sulfurtransferase purification steps. This figure clearly shows the various purification steps demonstrating the obtaining of the 3-mercaptopyruvate sulfurtransferase purified to homogeneity.

Example 2: Removal of the Sulfite Present in White Wine

The 3-mercaptopyruvate sulfurtransferase used was the D17A mutant of the purified *Escherichia coli* 3-mercaptopyruvate sulfurtransferase obtained in example 1 above.

The study was carried out with a dry white wine (Colombard Sauvignon, Côte de Gascogne, 44330 La chapelle Heulin, France). The sulfite concentration in this wine was measured at 160 mg/l before treatment using the sulfite oxidase kit (SO kit) (Megazyme International, Ireland) (black curve, FIG. 4). The amount of sulfite is given by the difference in optical density at 340 nm ($\Delta OD340$ nm) measured using a spectrophotometer (SAFAS UVmc$^2$).

Figure 3:
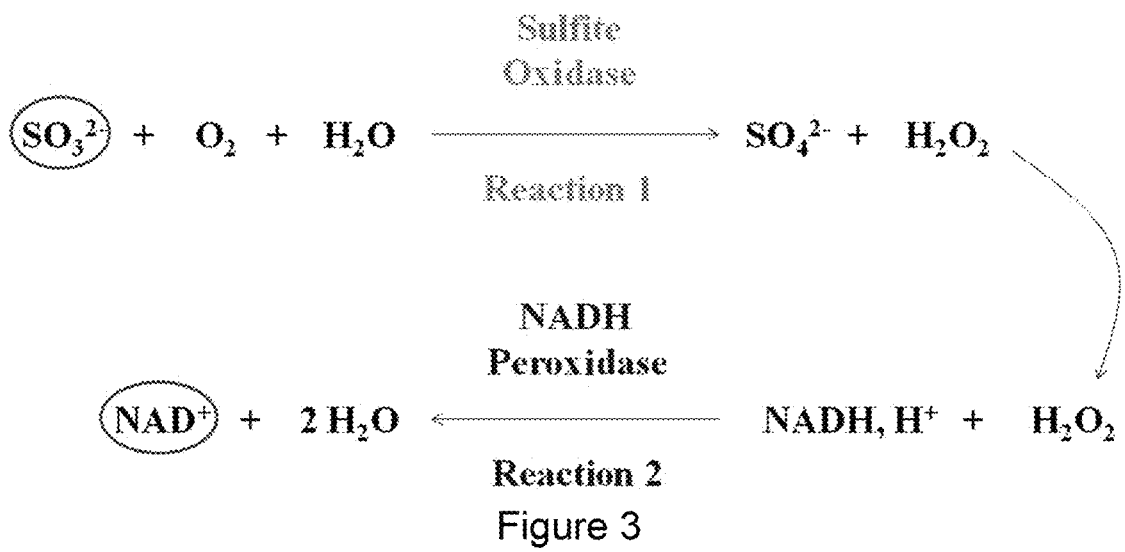
FIG. 3 is a simplified scheme representing the principle of the SO kit comprising the use of two enzymes, each catalyzing a reaction step. The first step involves sulfite oxidase (reaction 1) and the second involves NADH peroxidase (reaction 2).

The optical density was measured at 340 nm since it makes it possible to monitor the amount of NADH oxidized to NAD$^+$ (reaction 2, FIG. 3) which correlates with the amount of sulfite converted into sulfate (reaction 1, FIG. 3). In other words, the decrease in the optical density corresponds to the oxidation of the sulfites by sulfite oxidase, thus demonstrating the presence of sulfite.

The SO kit makes it possible to assay the amount of total sulfites in the wine, that is to say the free sulfites and the sulfites combined with organic molecules. Said method has the advantage of removing the total sulfites; in point of fact, the forms combined once in the stomach at a pH of 1.5 to 5 are released and constitute a not insignificant source of sulfite in the organism that it is necessary to eliminate. If the method makes it possible to remove the total sulfites, that means that the removal of the free sulfite forms results in a shift in the chemical equilibrium toward the decombination of the bound sulfites and thus, in the end, in the total removal of the sulfites (Grignard et al., 1950, Traité de chimie organique [Treatise on organic chemistry [14]).

Figure 4:
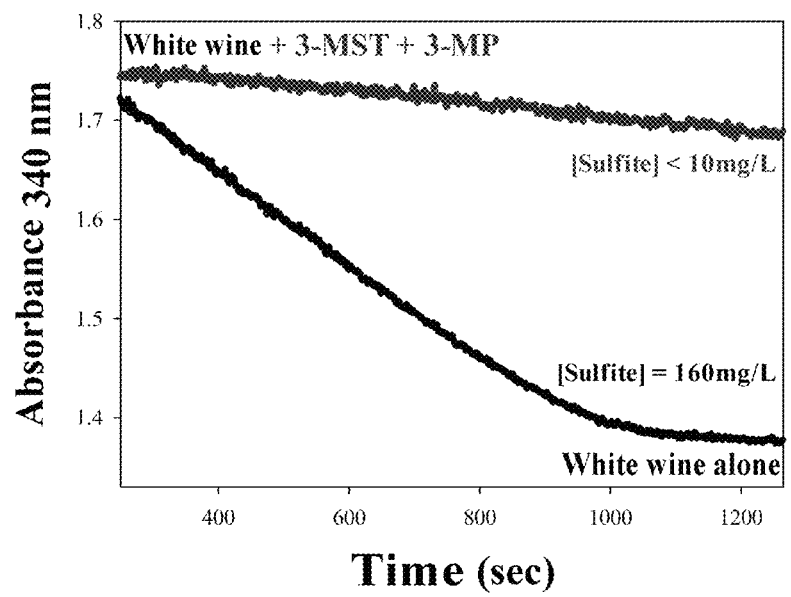
FIG. 4 represents the monitoring of the absorbance at 340 nm as a function of time of an untreated white wine sample (black curve white wine alone) and of a white wine sample after treatment with 2 µM of 3-mercaptopyruvate sulfurtransferase and a stoichiometric (1:1) amount of 3-mercaptopyruvate relative to the sulfites (upper curve white wine+3-MST+3-MP).

In order to determine whether the 3-mercaptopyruvate sulfurtransferase effectively makes it possible to convert the sulfite into thiosulfate, 25 ml of white wine were mixed with 2 µM of 3-mercaptopyruvate sulfurtransferase and 3-mercaptopyruvate in stoichiometry of 1:1 relative to the sulfite. The whole mixture was incubated for 5 min at a temperature of 25° C. and the optical density at 340 nm was measured. FIG. 4 presents the results obtained.

Figure 5:
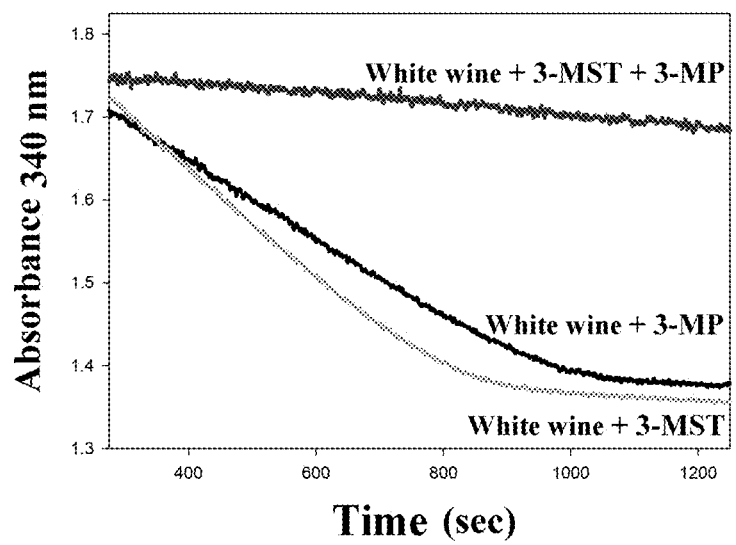
FIG. 5 represents the monitoring of the absorbance at 340 nm as a function of time of a white wine sample after treatment with a stoichiometric (1:1) amount of 3-mercaptopyruvate relative to the sulfites (black curve white wine alone), of a white wine sample after treatment with 2 µM of 3-mercaptopyruvate sulfurtransferase (white wine+3-MST) and of a white wine sample after treatment with 2 µM of 3-mercaptopyruvate sulfurtransferase and a stoichiometric (1:1) amount of 3-mercaptopyruvate relative to the sulfites (upper curve white wine+3-MST+3-MP).

The optical density was measured and there is no longer any decrease in the absorbance, attesting to a total removal of the sulfite present in the wine, demonstrating the conversion of the sulfite into thiosulfate (curve white wine+3-MST+3-MP, FIG. 4). Various controls show that the removal of the sulfite is indeed linked to the enzymatic activity of the enzyme, since the same experiment carried out in the absence of the 3-mercaptopyruvate substrate or in the absence of enzyme does not bring about a drop in the amount of sulfite in the wine. The results obtained are represented in FIG. 5 (respectively, curves white wine+3-MST and white wine+3-MP).

The removal of the free sulfites from white wine was also demonstrated by using strips (Quantofix (registered trade mark) Sulfite, Macherey-Nagel) (results not disclosed).

On the other hand, the amount of sulfite after the method could not be determined by the conventional methods currently used in the wine making industry, such as:

a. the Franz Paul method since it requires strong and aggressive acidification by adding sulfuric acid and heating, which under these conditions results in the dismutation of the thiosulfate to sulfite, b. the use of chemical kits since they contain reagents specific for thiol groups; in point of fact, the thiosulfate and the enzyme have thiolate groups which constitute a source of "parasitic" reactions that distort the measurement.

The assaying of sulfite after the implementation of an example method in accordance with the present invention was carried out using the SO kit (Megazyme International, Ireland) which constitutes a quantitative specific assaying method, and using strips (Quantofix (registered trade mark) Sulfite, Macherey-Nagel) making it possible to validate this method as a qualitative test.

As mentioned above, the SO kit makes it possible to assay the amount of total sulfites in the wine, that is to say the free sulfites and the sulfites combined with organic molecules. This assaying was carried out according to the recommended protocol in a glass vessel by mixing 1.3 ml of distilled water, 250 µl of buffer, 100 µl of sample studied, 100 µl of NADH and 10 µl of NADH peroxidase. After stabilization of the absorbance, 10 µl of sulfite oxidase were added and the variation in absorbance at 340 nm was measured.

In order to determine the optimal concentration of 3-mercaptopyruvate sulfurtransferase to be used, tests were carried out in the presence of 3-mercaptopyruvate in a stoichiometric amount relative to the sulfites and of variable concentrations of 3-mercaptopyruvate sulfurtransferase. The optical density at 340 nm was measured instantaneously following the reaction mixed.

The concentration of sulfite in the white wine sample was 160 mg/l. A measurement of the residual sulfite concentration after implementation of the method was carried out using the SO kit. The results obtained in the presence of various concentrations of 3-mercaptopyruvate sulfurtransferase are presented in table 1 below and in FIG. 5.

TABLE 1

Residual amount of sulfite as a function of 3-mercaptopyruvate sulfurtransferase concentration

| | Concentration of enzyme (3-MST) in nM | | | | |
|---|---|---|---|---|---|
| | 100 | 250 | 350 | 450 | 500 |
| Concentration of residual sulfite (mg/l) | 160 | 96 | 50 | 25 | <10 |

As demonstrated above, the 3-mercaptopyruvate sulfurtransferase makes it possible to remove the sulfites present in the white wine and a concentration of 500 nM of enzyme makes it possible to remove all the sulfites present.

Additionally, tests in the presence of variable concentrations of 3-mercaptopyruvate and of 500 nM of 3-mercaptopyruvate sulfurtransferase were carried out on a white wine sample. In particular, 3-mercaptopyruvate/sulfite molar ratios of 1/4, 1/2 and 3/4 were tested. A measurement of the residual sulfite concentration after implementation of the method was carried out using the SO kit. The results obtained in the presence of various concentrations of 3-mercaptopyruvate are presented in table 2 below and in FIG. 6.

TABLE 2

Residual amount of sulfite as a function of 3-mercaptopyruvate concentration

| | Percentage of 3-mercaptopyruvate/sulfite (mol/mol) | | | | |
|---|---|---|---|---|---|
| | 0 | 25 | 50 | 75 | 95 | 100 |
| Residual sulfite concentration (mg/l) | 168 | 112 | 86 | 46 | 13.4 | <10 |

Figure 6:
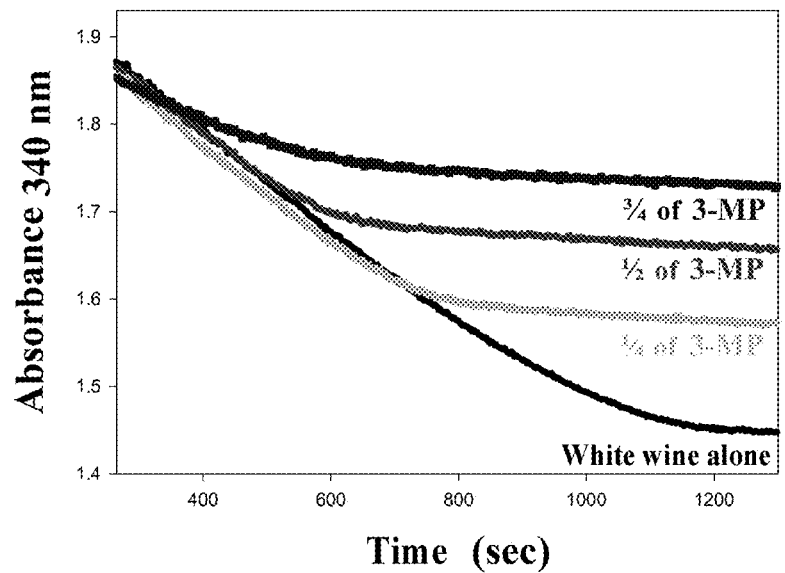
FIG. 6 represents the monitoring of the absorbance at 340 nm as a function of time of an untreated white wine sample (black curve white wine alone), of white wine samples after treatment with 2 µM of 3-mercaptopyruvate sulfurtransferase and a 3-mercaptopyruvate/sulfite ratio equal to 1/4 (curve 1/4 of 3-MP), to 1/2 of (curve 1/2 of 3-MP) and to 3/4 (curve 3/4 of 3-MP).

As demonstrated in table 2 above and in FIG. 6, the method according to the invention also advantageously makes it possible to control the final sulfite concentration.

In other words, the method according to the invention advantageously makes it possible to modify the sulfite concentration in a composition/sample to a given value or to eliminate/convert the sulfites present in a composition, for example wine.

Figure 7:
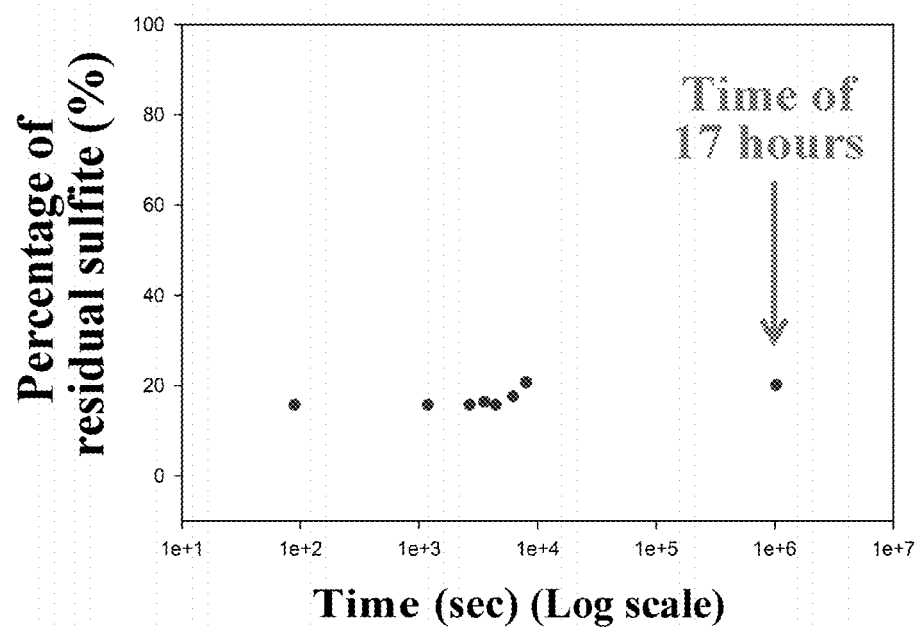
FIG. 7 is a graph representing the percentage of residual sulfite after treatment with said process (y-axis) as a function of time (x-axis).

Finally, thiosulfate is a chemically stable molecule. A verification of its stability in wine was carried out. For that, the residual amount of sulfite after treatment was measured as a function of time according to the following method: once the removal method had been applied to a volume of 25 ml of wine according to the same protocol as described above (500 nM 3-mercaptopyruvate sulfurtransferase, with a stoichiometric amount of 3-mercaptopyruvate/sulfite), the sample was stored at ambient temperature for 2 weeks and the amount of residual sulfate was quantified at regular time intervals, namely every three days. The results obtained show that, over a period of 17 h (or two weeks, results not shown), there is no release of sulfite by dismutation of the thiosulfate in the wine (FIG. 7).

In other words, a method in accordance with the present invention makes it possible to remove the sulfites by modifying them into thiosulfates in a composition, the modification being stable over time.

Example 3: Removal of the Sulfite in Red Wine

In the present example, the composition was red wine (Corbières, France). Since the tannins present in red wine interfere with the sulfite quantification method (SO kit mentioned above), it was necessary to remove them in order to demonstrate the disappearance of the sulfite in the composition.

The method for removing the sulfites was carried out on red wine according to the following protocol: 500 nM of 3-mercaptopyruvate sulfurtransferase, stoichiometric amount of 3-mercaptopyruvate/sulfite present in this wine. The tannins were removed by precipitation in the presence of polyvinylpolypyrollidone (PVPP) according to the following method: 10 ml of red wine sample were treated with 0.2 g of PVPP and a centrifugation at 4000 g was carried out for 5 minutes. This step was repeated 3 times.

Figure 8:
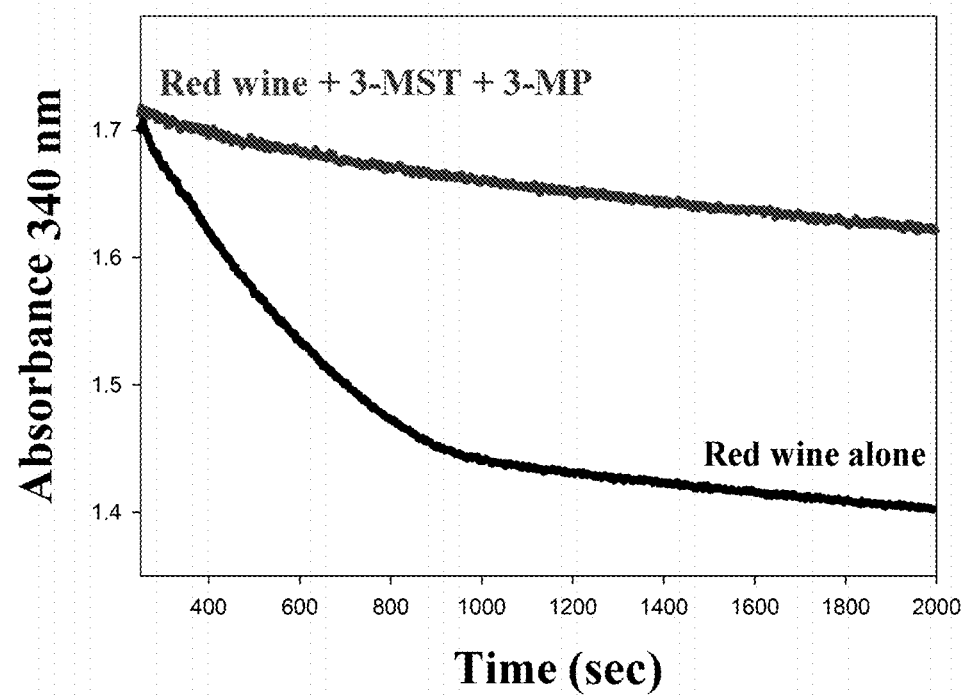
FIG. 8 represents the monitoring of the absorbance at 340 nm as a function of time of an untreated red wine sample (black curve red wine alone) and of a red wine sample after treatment with 0.5 µM of 3-mercaptopyruvate sulfurtransferase and a stoichiometric (1:1) amount of 3-mercaptopyruvate relative to the sulfites (upper curve red wine+3-MST+3-MP).

A measurement of the sulfite concentration before and after implementation of the method was carried out using the SO kit according to the same protocol as described in example 1. The results obtained are presented in FIG. 8. The sulfite concentration in the red wine was 100 mg/l (black curve red wine alone). The addition of 500 nM of 3-mercaptopyruvate sulfurtransferase and of a stoichiometric amount of 3-mercaptopyruvate made it possible to remove the sulfite (upper curve red wine+3-MST+3-MP).

This example clearly demonstrates that a method according to the invention makes it possible to remove the sulfites present in red wine.

Example 4: Removal of the Sulfite in an Anesthetic

In this example, the composition was a local anesthetic (Septanest (registered trade mark)) 40 mg/ml, with adrenalin at 1/100 000, articaine Chl., 40 mg/l, Laboratoire Septodont).

The method for removing the sulfites from the composition was carried out according to the following protocol: 500 nM of 3-mercaptopyruvate sulfurtransferase, stoichiometric amount of 3-mercaptopyruvate/sulfite present in the composition.

The sulfite concentration before and after implementation of the method was measured using the SO kit according to the same protocol as described in example 1. The results obtained are presented in FIG. 9. The sulfite concentration in the composition was 410 mg/l (curve 0 3-MP/sulfite). The addition of 500 nM of 3-mercaptopyruvate sulfurtransferase and of a stoichiometric amount of 3-mercaptopyruvate allowed the total removal of the sulfite present in the composition (curve Septanest+3-MST+3-MP) in accordance with the present invention.

Figure 9:
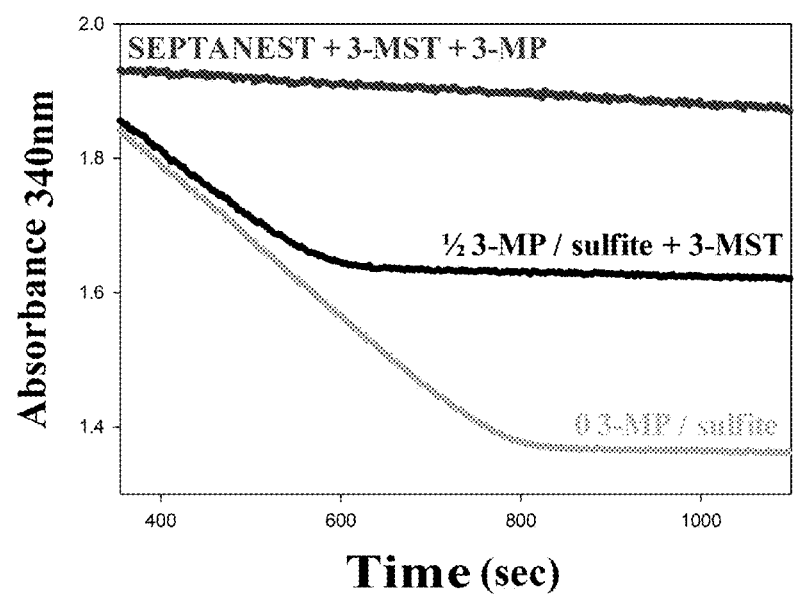
FIG. 9 represents the monitoring of the absorbance at 340 nm as a function of time of a local anesthetic (Septanest (registered trade mark)) after treatment with 0.5 µM of 3-mercaptopyruvate sulfurtransferase and 3-mercaptopyruvate with a 3-mercaptopyruvate/sulfite ratio equal to 0 (curve 0 3-MP/sulfite), to 1/2 (curve 1/2 of 3-MP/sulfite) and to 1 (curve Septanest+3-MST+3-MP).

In addition, the method was carried out with a 1/2 ratio of 3-mercaptopyruvate/sulfite (mol/mol) (FIG. 9, curve 1/2 of 3-MP/sulfite). As demonstrated, half the sulfites present in the composition are converted into thiosulfate.

This example thus clearly demonstrates that a method in accordance with the present invention makes it possible to treat pharmaceutical compositions in order to reduce the amount of sulfite present.

LIST OF REFERENCES

1. Shih et al., 1977, The New England Journal of Medicine.
2. Andersson et al., 2013, International Archives of Occupational and Environmental Health.
3. Ozsoy et al., 2014, Toxicology and Industrial Health.
4. WO 2015/051187.
5. Hermann et al., 2015, "The octahaem MccA is a haem c-copper sulfite reductase" Nature 520, 706-709
6. http://www.promega.com/vectors/mammalian_express-_vectors.htm.
7. http://www.qiagen.com/overview/qiagenes.aspx?gaw= PROTQIAgenes0807&gkw=mammalian+expression
8. http://www.scbt.com/chap_exp_vectors.php?type= pCruzTM%20Expression%20Vectors.
9. WO 83/004261
10. Beutler, H. O., 1988, Sulphite In Methods of Enzymatic Analysis.
11. Bondet and Sylvestre, 2005, Pratiquer les contrôles en œnologie [Carrying out tests in enology].
12. FDA report regarding sodium thiosulfate, SCOGS-52, 1975.

13. Arrestier et al., 2016, Medicine, 95 (6).
14. Grignard et al., 1950, Traitè de chimie organique [Treatise on organic chemistry], 769-770.

The invention claimed is:

1. A method for treating a composition, comprising introducing into said composition 3-mercaptopyruvate sulfurtransferase (3-MST) and a substrate of said 3-mercaptopyruvate sulfurtransferase in order to convert sulfites in the composition into thiosulfates, wherein the composition is an agri-food, pharmaceutical, cosmetic or veterinary composition.

2. A method for converting sulfite present in a composition into thiosulfate, comprising introducing into said composition 3-mercaptopyruvate sulfurtransferase (3-MST) and of a substrate of said 3-mercaptopyruvate sulfurtransferase and converting the sulfite present in the composition into thiosulfate, wherein the composition is an agri-food, pharmaceutical, cosmetic or veterinary composition.

3. The method as claimed in claim 1, wherein said 3-mercaptopyruvate sulfurtransferase is recombinant.

4. The method as claimed in claim 1, wherein said 3-mercaptopyruvate sulfurtransferase comprises, in its peptide sequence, the following three sequences:

$RX_aWWM$ (SEQ ID No. 13)

$CGSGVTAX_b$ (SEQ ID No. 14)

$GHIX_cG$ (SEQ ID No. 15)

wherein $X_a$ is A, V or L, $X_b$ is A or C, and $X_c$ is P or E.

5. The method as claimed in claim 1, wherein said 3-mercaptopyruvate sulfurtransferase is from *Escherichia coli*.

6. The method as claimed in claim 1, wherein the 3-mercaptopyruvate sulfurtransferase is a protein or peptide sequence selected from the group SEQ ID Nos 2, 5, 6 and 7.

7. The method as claimed in claim 1, wherein said substrate of said 3-mercaptopyruvate sulfurtransferase is 3-mercaptopyruvate.

8. The method as claimed in claim 1, wherein the stoichiometric ratio of said substrate to the sulfite present in said composition is at most 1:1.

9. The method as claimed in claim 2, wherein said 3-mercaptopyruvate sulfurtransferase is recombinant.

10. The method as claimed in claim 2, wherein said 3-mercaptopyruvate sulfurtransferase comprises, in its peptide sequence, the following three sequences:

RX$_a$WWM (SEQ ID No. 13)

CGSGVTAX$_b$ (SEQ ID No. 14)

GHIX$_c$G (SEQ ID No. 15)

wherein X$_a$ is A, V or L, X$_b$ is A or C, and X$_c$ is P or E.

11. The method as claimed in claim 2, wherein said 3-mercaptopyruvate sulfurtransferase is from *Escherichia coli*.

12. The method as claimed in claim 2, wherein the 3-mercaptopyruvate sulfurtransferase is a protein or peptide sequence selected from the group SEQ ID Nos 2, 5, 6 and 7.

13. The method as claimed in claim 2, wherein the composition is an agri-food, pharmaceutical, cosmetic or veterinary composition.

14. The method as claimed in claim 2, wherein said substrate of said 3-mercaptopyruvate sulfurtransferase is 3-mercaptopyruvate.

15. The method as claimed in claim 2, wherein the stoichiometric ratio of said substrate to the sulfite present in said composition is at most 1:1.

* * * * *